United States Patent [19]

Mobarry

[11] 4,350,166

[45] Sep. 21, 1982

[54] APNEA DETECTOR

[75] Inventor: John W. Mobarry, Edina, Minn.

[73] Assignee: Honeywell Inc., Minneapolis, Minn.

[21] Appl. No.: 216,030

[22] Filed: Dec. 12, 1980

[51] Int. Cl.³ ............................................... A61B 5/08
[52] U.S. Cl. .................................. 128/664; 128/719;
128/716
[58] Field of Search ....................... 128/664, 716, 719;
340/573, 575

[56] References Cited

U.S. PATENT DOCUMENTS 4,011,859  3/1977  Frankenberger ................ 128/719
4,289,142  9/1981  Kearns ............................. 128/716

FOREIGN PATENT DOCUMENTS 2813518  5/1979  Fed. Rep. of Germany ...... 128/719

OTHER PUBLICATIONS

AGA Publication #556.005, AGA Aktiebolag, Lindingö, Sweden, 1973.

Primary Examiner—Kyle L. Howell
Assistant Examiner—John C. Hanley
Attorney, Agent, or Firm—Lockwood D. Burton; Mitchell J. Halista

[57] ABSTRACT

A non-contacting apnea detector includes a long wave infrared detecting device which is arranged with a focusing means to define a predetermined field of view. This detector is positioned to include the infant or at least the head and shoulder portion of the infant in that field of view. The exhalations of the infant include large quantities of carbon dioxide. Carbon dioxide is absorbent to the long wave infrared radiation. The detector detects the difference in the infrared radiation due to the absorption incident to the exhalations of the infant. The resulting signal is applied to a suitable alarm circuit to indicate an interruption of the exhalation exceeding a predetermined time interval.

8 Claims, 2 Drawing Figures 4,350,166

APNEA DETECTOR

BACKGROUND OF THE INVENTION

The present invention relates to medical instrumentation. More particularly it relates to improved apnea detector.

There has been, in recent years, an increasing awareness of the incidence as what is now known as sudden infant death syndrome, or crib death. In some instances, this tragedy has been attributed to apnea, or a cessation of breathing, of the infant. There have been many devices proposed for the detection of such apena, most if not all of which require attachment to the infant in the crib. Some of these devices have been in the nature of sensors positioned to be in the flow of the exhalation of the infant to thereby detect the continuity of the breathing process. Other techniques have involved the use of a sphygmomanometer of one sort of another to measure the body movements of the infant incident to the breathing process. These of necessity require attachement to the infant. As long as the apparatus is attached to the infant, a measure of inconvenience or discomfort is a concomitant of the apparatus. Additionally, the sphygmomanometer can under certain conditions give a false indication of continued breathing when actual breathing has stopped. For example, if the infant has stopped breathing due to a blockage of the breathing passageways, and the chest of the infant continues to heave in a spasmotic effort to reestablish breathing, a false sense of continued breathing will be recorded by such motion sensing devices.

SUMMARY OF THE INVENTION

It is, accordingly an object of the present invention to provide an improved apnea detector which obviates the shortcomings of the previous devices.

It is another object of the present invention to provide an improved non-contacting apnea detector.

In accomplishing these and other objects, there has been provided, in accordance with the present invention, a non-contacting apnea detector wherein a long wave infrared detecting device is arranged with a focusing means to define a predetermined field of view. This detector is positioned to include the infant or at least the head and shoulder portion of the infant in that field of view. The exhalations of the infant include large quantities of carbon dioxide. Carbon dioxide is absorbent to the long wave infrared radiation. The detector detects the difference in the infrared radiation due to the absorption incident to the exhalations of the infant. The resulting signal is applied to a suitable alarm circuit to indicate an interruption of the exhalation exceeding a predetermined time interval.

BRIEF DESCRIPTION OF THE DRAWINGS

A better understanding of the present invention may be had from the following detailed description when read in the light of the accompanying drawings in which.

DETAILED DESCRIPTION

Figure 1:
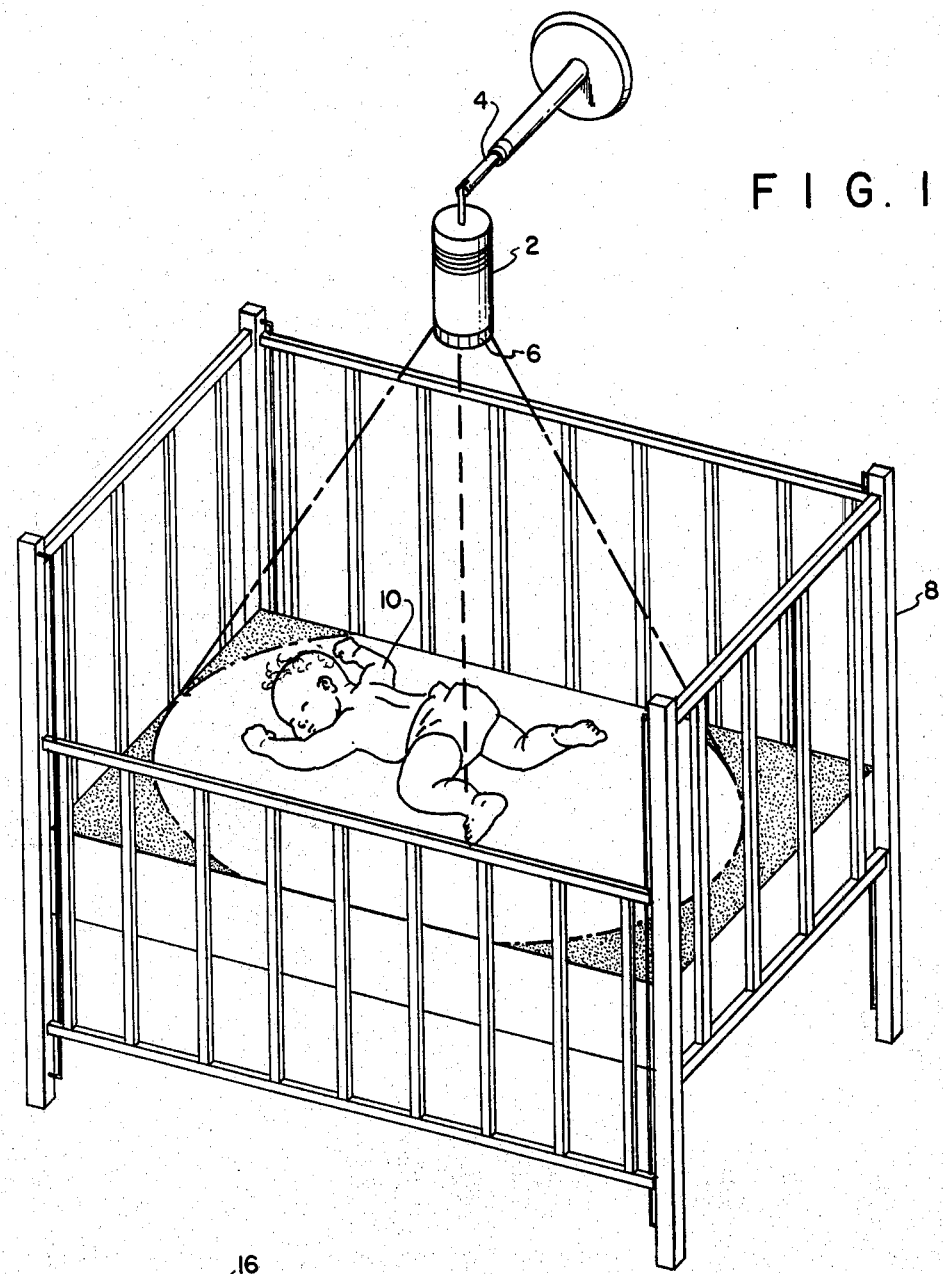
FIG. 1 is a pictorial representation of an apnea detector embodying the present invention.

Referring now to the drawings in more detail, there is shown in FIG. 1 a non-contacting apnea detector which is in the form of a long wave infrared detector array mounted in a housing member 2. The housing member 2 is supported from the wall of the room or from the ceiling of the room. Th bracket 4 is is the form of an djustable length arm preferably of the telescoping type. The lower end of the housing member 2 includes a focusing ring 6 which may be adjusted to adapt the cone angle of the field of view of the sensor to a desired or optimum area. The focusing ring may include, for example, a spatial filter such as a positionally adjustable aperture plate or an adjustable iris diaphragm.

The detector housing 2 is positioned over a crib 8 in which the infant 10 is placed. The field of view defined by the adjustments of the focusing rings 6 may include the entire surface of the crib; however, for a better signal-to-noise ratio, a smaller field of view embracing only the infant would be more desirable.

Figure 2:
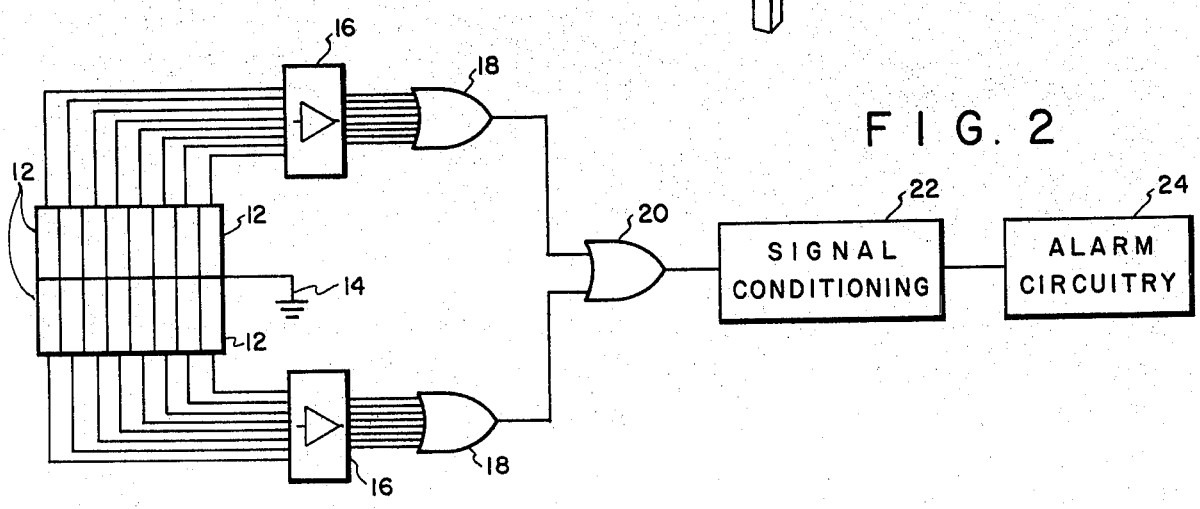
FIG. 2 is a block diagram of a suitable circuit arrangement for use in connection with the present invention.

In FIG. 2 there is shown a representative circuit diagram such as may be used in the practice of the present invention.

There is shown an array of two sets of infrared sensors 12, each array having eight sensors therein. Each of the sensors is connected between a reference point such as ground 14 and the input of an amplifier module 16. A separate eight-input amplifier module 16 is shown for each of the two arrays. Thus, each of the sensor elements 12 has a separate input to the amplifier modules 16. There are, accordingly, eight output leads from each of the two amplifier modules 16 each representing the amplification of the signal applied from one of the sensors 12. The output leads from the amplifier modules are applied to corresponding input terminals of two associated eight-input OR-gates 18. The output signals from the OR-gates 18 are applied to the two input terminals of a further OR-gate 20. The output of the OR-gate 20 is applied to the input of signal conditioning circuit 22 the output of which is, in turn, applied to the input of an alarm circuitry 24.

While in FIG. 2, th circuit has been illustrated as including an array of a plurality of infrared sensor elements 12, it will be appreciated that a unitary infrared detector cell may be used.

Suitable circuit structure for use as the signal conditioning circuit 22 and the alarm circuitry 24 are themselves, well known in the art as represented, for example, in Strube U.S. Pat. No. 4,169,462. While that patent relates to motion responsive circuit, the signal conditioning and alarm circuitry may be representative of the type of circuit suitable for use in connection with the present invention.

The infrared detector units may be either of the lead titanate/barium titanate ceramic type or of the $PVF_2$ (polyvinyledene fluoride) plastic type. The response characteristic of such infrared sensors is a function of a differential in temperature with respect to time. Thus for a steady state temperature pattern, no signal is generated by the infrared sensors. On the other hand, the exhalations of the infant contain a large quantity of carbon dioxide. Carbon dioxide is, in turn, highly absorptive of infrared radiations. Therefore the steady state infrared emitted from the infant and its environs is periodically modulated by the exhaled carbon dioxide. This modulation of the infrared radiation is sensed by the infrared sensors to produce a periodic signal. The accompanying circuitry responds to these periodic signals to prevent the issuance of an alarm signal. If there is an interruption to the periodicity of the modulation signals, the alarm circuitry responds by issuing an alarm signal. It has been determined that interruptions in breathing, and thus interruptions in the periodic signal from the sensor, could occur occasionally for nearly 20 seconds with normal, healthy subjects. If the periodic signal, i.e breathing, stops for more than 20 seconds, the alarm will sound, alerting an attendant, presumably a parent, who may then immediately take corrective measures to restore a breathing pattern in the infant. While the invention has been described as to relating to an infant, it is readily apparent that the same apparatus may also be used in connection with adults who have experienced or potentially may experience apnea.

Inasmuch as the sensor of the present invention responds to the modulation of the ambient infrared by the carbon dioxide content of the exhalation, the device is responsive directly to the breathing process. It is not dependent upon body motions normally incident to breathing. Thus a more reliable apnea detection is provided which is directly sensitive to the breathing process and is not dependent upon potentially spurious body motions as an indication of apnea. Additionally with the detector being completely remote from and detached from the subject, there is no body contact with that subject which could provide a potentially uncomfortable or dangerous physical engagement with that individual. Thus there has been provided in accordance with the present invention, an improved non-contacting, highly reliable apnea detector.

The embodiments of the invention in which an exclusive property or privilege are claimed is defined as follows:

1. An apnea detector for monitoring the respiration of a monitored subject, said apnea detector comprising:
    an infrared radiation detector means;
    means for defining a field of view for said radiation detector means, said field of view defining means being arranged to include an area of said monitored subject in said field of view containing exhalation products from said monitored subject;
    mounting means positioning said radiation detector means spaced from said monitored subject in a non-contacting relationship to be responsive to modulations of ambient infrared radiation produced by exhalation products from said monitored subject to produce a corresponding modulation signal; and
    alarm means responsive to a prolonged interruption of said modulation signal produced by an interruption of the respiration of said monitored subject to effect an alarm signal indicative of apnea.

2. An apnea detector as set forth in claim 1 wherein said exhalation products contain carbon dioxide which produces an absorption of said ambient infrared radiation.

3. An apnea detector as set forth in claim 1 wherein said infrared radiation detector means comprises a unitary detector cell, and means connecting said cell to said alarm means.

4. An apnea detector as set forth in claim 3 wherein said means connecting said cell to said alarm means includes an amplifier means.

5. An apnea detector as set forth in claim 1 wherein said infrared radiation detector means comprises a plurality of individual detector cells, and
    means connecting each of said cells individually to said alarm means.

6. An apnea detector as set forth in claim 5 wherein said means connecting each of said cells to said alarm means comprises amplifier means and gating means.

7. An apnea detector as set forth in claim 6 wherein said gating means comprises OR-gates to individually connect those cells producing a modulation signal to said alarm means whereby to enhance the signal-to-noise ratio of said apnea detector.

8. An apnea detector as set forth in claim 1 wherein said mounting means includes a mounting bracket having an adjustable support arm for adjustably positioning said detector means relative to said monitored subject.

* * * * *